US007066951B2

(12) United States Patent
Chobotov

(10) Patent No.: US 7,066,951 B2
(45) Date of Patent: Jun. 27, 2006

(54) DELIVERY SYSTEM AND METHOD FOR EXPANDABLE INTRACORPOREAL DEVICE

(75) Inventor: Michael V. Chobotov, Santa Rosa, CA (US)

(73) Assignee: TriVascular, Inc., Santa Rosa, CA (US)

( * ) Notice: Subject to any disclaimer, the term of this patent is extended or adjusted under 35 U.S.C. 154(b) by 0 days.

(21) Appl. No.: 10/419,312

(22) Filed: Apr. 17, 2003

(65) Prior Publication Data

US 2003/0220681 A1 Nov. 27, 2003

Related U.S. Application Data

(62) Division of application No. 09/774,733, filed on Jan. 31, 2001, now Pat. No. 6,602,280.
(60) Provisional application No. 60/179,812, filed on Feb. 2, 2000.

(51) Int. Cl.
*A61F 2/06* (2006.01)

(52) U.S. Cl. ..................................... 623/1.12; 623/1.25
(58) Field of Classification Search ................ 623/1.11, 623/1.12, 1.25; 606/108, 194, 195
See application file for complete search history.

(56) References Cited

U.S. PATENT DOCUMENTS 3,657,744 A    4/1972   Ersek (Continued)

FOREIGN PATENT DOCUMENTS

EP          0 646 365 A1     4/1995

(Continued)

OTHER PUBLICATIONS

US 6,413,270, 7/2002, Thornton et al. (withdrawn)

Lawrence, Jr. et al., "Percutaneous Endovascular Graft: Experimental Evaluation," *Radiology*, 163/2:357–360 (1987).

Mirich et al., "Percutaneously Placed Endovascular Grafts for Aortic Aneurysms: Feasibilty Study," *Radiology*, 170/3:1022–1037 (1989).

Cooley, Denton A., *Surgical Treatment of Aortic Aneurysms* (Book), W.B. Saunders Company, West Washington Square, PA (1986).

AneuRX Stent Graft brochure, "An Innovative Modular Approach for the Treatment of Abdominal Aortic Aneurysms (AAA)," *Medtronic*.

*Primary Examiner*—Bruce E Snow
(74) *Attorney, Agent, or Firm*—RatnerPrestia

(57) ABSTRACT

A catheter for delivery of an expandable intracorporeal device and method of using the catheter. The catheter may have an elongate shaft with a proximal section, distal section, proximal end and distal end. The distal section has a radially expandable shear barrier which is at least partially radially constrained by an outer radially constraining section. An expandable intracorporeal device, specifically an expandable endovascular graft, is disposed within an inner space within the radially expandable shear barrier. The catheter is guided to a desired site within a patient's body and the radial constraint of the outer radially constraining section is at least partially removed from the radially expandable shear barrier so as to allow the shear barrier and expandable intracorporeal device to expand and deploy. Typically, the radial constraint of the outer radially constraining section is carried out by relative axial movement between the outer radially constraining section and the radially expandable shear barrier.

12 Claims, 10 Drawing Sheets

U.S. PATENT DOCUMENTS

| | | |
|---|---|---|
| 4,140,126 A | 2/1979 | Choudhury |
| 4,562,596 A | 1/1986 | Kornberg |
| 4,577,631 A | 3/1986 | Kreamer |
| 4,580,568 A | 4/1986 | Gianturco |
| 4,787,899 A | 11/1988 | Lazarus |
| 5,104,399 A | 4/1992 | Lazarus |
| 5,151,105 A | 9/1992 | Kwan-Gett |
| 5,156,620 A | 10/1992 | Pigott |
| 5,275,622 A | 1/1994 | Lazarus et al. |
| 5,344,426 A | 9/1994 | Lau et al. |
| 5,354,329 A | 10/1994 | Whalen |
| 5,360,443 A | 11/1994 | Barone et al. |
| 5,387,235 A | 2/1995 | Chuter et al. |
| 5,397,345 A | 3/1995 | Lazarus |
| 5,456,694 A | 10/1995 | Marin et al. |
| 5,456,713 A | 10/1995 | Chuter |
| 5,464,449 A | 11/1995 | Ryan et al. |
| 5,480,423 A | 1/1996 | Ravenscroft et al. |
| 5,489,295 A | 2/1996 | Piplani et al. |
| 5,507,769 A | 4/1996 | Marin et al. |
| 5,522,880 A | 6/1996 | Barone et al. |
| 5,522,883 A | 6/1996 | Slater et al. |
| 5,562,724 A | 10/1996 | Vorwerk et al. |
| 5,562,726 A | 10/1996 | Chuter |
| 5,562,728 A | 10/1996 | Lazarus et al. |
| 5,578,071 A | 11/1996 | Parodi |
| 5,578,072 A | 11/1996 | Barone et al. |
| 5,591,229 A | 1/1997 | Parodi |
| 5,609,625 A | 3/1997 | Piplani et al. |
| 5,609,627 A | 3/1997 | Goicoechea et al. |
| 5,626,599 A | 5/1997 | Bourne et al. |
| 5,628,783 A | 5/1997 | Quiachon et al. |
| 5,632,772 A | 5/1997 | Alcime et al. |
| 5,639,278 A | 6/1997 | Dereume et al. |
| 5,662,675 A | 9/1997 | Polanskyj Stockert |
| 5,662,700 A | 9/1997 | Lazarus |
| 5,665,115 A | 9/1997 | Cragg |
| 5,669,936 A | 9/1997 | Lazarus |
| 5,676,671 A | 10/1997 | Inoue |
| 5,676,696 A | 10/1997 | Marcade |
| 5,676,697 A | 10/1997 | McDonald |
| 5,683,449 A | 11/1997 | Marcade |
| 5,683,451 A * | 11/1997 | Lenker et al. ............ 623/1.11 |
| 5,690,644 A | 11/1997 | Yurek et al. |
| 5,693,083 A | 12/1997 | Baker et al. |
| 5,693,084 A | 12/1997 | Chuter |
| 5,693,087 A | 12/1997 | Parodi |
| 5,693,088 A | 12/1997 | Lazarus |
| 5,709,701 A | 1/1998 | Parodi |
| 5,709,703 A | 1/1998 | Lukie et al. |
| 5,713,917 A | 2/1998 | Leonhardt et al. |
| 5,720,776 A | 2/1998 | Chuter et al. |
| 5,723,004 A | 3/1998 | Dereume et al. |
| 5,733,325 A | 3/1998 | Robinson et al. |
| 5,749,920 A | 5/1998 | Quiachon et al. |
| 5,749,921 A | 5/1998 | Lenker et al. |
| 5,766,203 A | 6/1998 | Imran et al. |
| 5,769,885 A | 6/1998 | Quiachon et al. |
| 5,769,887 A | 6/1998 | Brown et al. |
| 5,782,838 A | 7/1998 | Beyar et al. |
| 5,782,909 A | 7/1998 | Quiachon et al. |
| 5,800,518 A | 9/1998 | Piplani et al. |
| 5,824,039 A | 10/1998 | Piplani et al. |
| 5,824,041 A | 10/1998 | Lenker et al. |
| 5,824,044 A | 10/1998 | Quiachon et al. |
| 5,824,058 A | 10/1998 | Ravenscroft et al. |
| 5,833,707 A | 11/1998 | McIntyre et al. |
| 5,843,158 A | 12/1998 | Lenker et al. |
| 5,843,162 A | 12/1998 | Inoue |
| 5,843,167 A | 12/1998 | Dwyer et al. |
| 5,855,598 A | 1/1999 | Pinchuk |
| 5,871,536 A | 2/1999 | Lazarus |
| 5,873,906 A | 2/1999 | Lau et al. |
| 5,906,619 A | 5/1999 | Olson et al. |
| 5,919,204 A | 7/1999 | Lukie et al. |
| 5,944,750 A | 8/1999 | Tanner et al. |
| 5,954,729 A | 9/1999 | Bachmann et al. |
| 5,957,973 A | 9/1999 | Quiachon et al. |
| 5,968,068 A | 10/1999 | Dehdashtian et al. |
| 5,972,023 A | 10/1999 | Tanner et al. |
| 5,976,179 A | 11/1999 | Inoue |
| 5,976,650 A | 11/1999 | Campbell et al. |
| 5,984,964 A | 11/1999 | Roberts et al. |
| 5,993,481 A | 11/1999 | Marcade et al. |
| 6,001,123 A | 12/1999 | Lau |
| 6,004,347 A | 12/1999 | McNamara et al. |
| 6,004,348 A | 12/1999 | Banas et al. |
| 6,015,431 A | 1/2000 | Thornton et al. |
| 6,017,364 A | 1/2000 | Lazarus |
| 6,019,778 A | 2/2000 | Wilson et al. |
| 6,019,779 A | 2/2000 | Thorud et al. |
| 6,024,763 A | 2/2000 | Lenker et al. |
| 6,030,413 A | 2/2000 | Lazarus |
| 6,030,414 A | 2/2000 | Taheri |
| 6,036,413 A | 3/2000 | Chandrasekar |
| 6,036,702 A | 3/2000 | Bachinski et al. |
| 6,036,723 A | 3/2000 | Anidjar et al. |
| 6,036,725 A | 3/2000 | Avellanet |
| 6,039,758 A | 3/2000 | Quiachon et al. |
| 6,042,589 A | 3/2000 | Marianne |
| 6,042,605 A | 3/2000 | Martin et al. |
| 6,045,557 A | 4/2000 | White et al. |
| 6,051,020 A | 4/2000 | Goicoechea et al. |
| 6,059,821 A | 5/2000 | Anidjar et al. |
| 6,070,589 A | 6/2000 | Keith et al. |
| 6,077,297 A | 6/2000 | Robinson et al. |
| 6,090,128 A | 7/2000 | Douglas |
| 6,098,630 A | 8/2000 | Papazoglou |
| 6,110,198 A | 8/2000 | Fogarty et al. |
| 6,126,685 A | 10/2000 | Lenker et al. |
| 6,132,459 A | 10/2000 | Piplani et al. |
| 6,139,572 A | 10/2000 | Campbell et al. |
| 6,142,973 A | 11/2000 | Carleton et al. |
| 6,143,014 A | 11/2000 | Dehdashtian et al. |
| 6,143,016 A | 11/2000 | Bleam et al. |
| 6,143,021 A | 11/2000 | Staehle et al. |
| 6,146,389 A | 11/2000 | Geitz |
| 6,152,944 A | 11/2000 | Holman et al. |
| 6,156,063 A | 12/2000 | Douglas |
| 6,159,229 A | 12/2000 | Jendersee et al. |
| 6,165,210 A | 12/2000 | Lau et al. |
| 6,165,213 A | 12/2000 | Goicoechea et al. |
| 6,165,214 A | 12/2000 | Lazarus |
| 6,168,610 B1 | 1/2001 | Marin et al. |
| 6,168,616 B1 | 1/2001 | Brown, III |
| 6,168,617 B1 | 1/2001 | Blaeser et al. |
| 6,168,618 B1 | 1/2001 | Frantzen |
| 6,168,620 B1 | 1/2001 | Kerr |
| 6,183,481 B1 | 2/2001 | Lee et al. |
| 6,183,504 B1 | 2/2001 | Inoue |
| 6,187,036 B1 | 2/2001 | Shaolian et al. |
| 6,193,745 B1 | 2/2001 | Fogarty et al. |
| 6,197,046 B1 | 3/2001 | Piplani et al. |
| 6,197,049 B1 | 3/2001 | Shaolian et al. |
| 6,200,339 B1 | 3/2001 | Leschinsky et al. |
| 6,203,550 B1 | 3/2001 | Olson |
| 6,203,568 B1 | 3/2001 | Lombardi et al. |
| 6,210,422 B1 | 4/2001 | Douglas |
| 6,210,434 B1 | 4/2001 | Quichon et al. |
| 6,210,435 B1 | 4/2001 | Piplani et al. |
| 6,214,038 B1 | 4/2001 | Piplani et al. |

| Patent | Date | Inventor |
|---|---|---|
| 6,224,609 B1 | 5/2001 | Ressemann et al. |
| 6,235,050 B1 | 5/2001 | Quiachon et al. |
| 6,235,051 B1 | 5/2001 | Murphy |
| 6,241,759 B1 | 6/2001 | Piplani et al. |
| 6,245,097 B1 | 6/2001 | Inoue |
| 6,251,132 B1 | 6/2001 | Ravenscroft et al. |
| 6,254,593 B1 | 7/2001 | Wilson |
| 6,258,073 B1 | 7/2001 | Mauch |
| 6,261,316 B1 | 7/2001 | Shaolian et al. |
| 6,261,317 B1 | 7/2001 | Inoue |
| 6,264,662 B1 | 7/2001 | Lauterjung |
| 6,280,466 B1 | 8/2001 | Kugler et al. |
| 6,283,991 B1 | 9/2001 | Cox et al. |
| 6,287,315 B1 | 9/2001 | Wijeratne et al. |
| 6,287,329 B1 | 9/2001 | Duerig et al. |
| 6,287,330 B1 | 9/2001 | Johansson et al. |
| 6,293,969 B1 | 9/2001 | Chuter |
| 6,302,891 B1 | 10/2001 | Nadal |
| 6,302,906 B1 | 10/2001 | Goicoechea et al. |
| 6,302,908 B1 | 10/2001 | Parodi |
| 6,306,145 B1 | 10/2001 | Leschinsky |
| 6,312,462 B1 | 11/2001 | McDermott et al. |
| 6,322,587 B1 | 11/2001 | Quiachon et al. |
| 6,325,819 B1 | 12/2001 | Pavcnik et al. |
| 6,325,825 B1 | 12/2001 | Kula et al. |
| 6,331,186 B1 | 12/2001 | Wang et al. |
| 6,331,190 B1 | 12/2001 | Shokoohi et al. |
| 6,331,191 B1 | 12/2001 | Chobotov |
| 6,344,044 B1 | 2/2002 | Fulkerson et al. |
| 6,344,054 B1 | 2/2002 | Parodi |
| 6,352,553 B1 | 3/2002 | Van der Burg et al. |
| 6,352,561 B1 | 3/2002 | Leopold et al. |
| 6,371,979 B1 | 4/2002 | Beyar et al. |
| 6,383,213 B1 | 5/2002 | Wilson et al. |
| 6,391,050 B1 | 5/2002 | Broome |
| 6,395,022 B1 | 5/2002 | Piplani et al. |
| 6,413,269 B1 | 7/2002 | Bui et al. |
| 6,416,535 B1 | 7/2002 | Lazarus |
| 6,416,536 B1 | 7/2002 | Yee |
| 6,416,542 B1 | 7/2002 | Marcade et al. |
| 6,425,898 B1 | 7/2002 | Wilson et al. |
| 6,428,566 B1 | 8/2002 | Holt |
| 6,428,567 B1 | 8/2002 | Wilson et al. |
| 6,432,129 B1 | 8/2002 | DiCaprio |
| 6,432,131 B1 | 8/2002 | Ravenscroft |
| 6,436,104 B1 | 8/2002 | Hojeibane |
| 6,443,979 B1 | 9/2002 | Stalker et al. |
| 6,447,501 B1 | 9/2002 | Solar et al. |
| 6,447,522 B1 | 9/2002 | Gambale et al. |
| 6,451,053 B1 | 9/2002 | Dehdashtian et al. |
| 6,464,721 B1 | 10/2002 | Marcade et al. |
| 6,471,718 B1 | 10/2002 | Staehle et al. |
| 6,471,722 B1 | 10/2002 | Inoue |
| 6,475,166 B1 | 11/2002 | Escano |
| 6,475,208 B1 | 11/2002 | Mauch |
| 6,478,807 B1 | 11/2002 | Foreman et al. |
| 6,485,515 B1 | 11/2002 | Strecker |
| 6,488,694 B1 | 12/2002 | Lau et al. |
| 6,488,700 B1 | 12/2002 | Klumb et al. |
| 6,488,701 B1 | 12/2002 | Nolting et al. |
| 6,494,875 B1 | 12/2002 | Mauch |
| 6,494,904 B1 | 12/2002 | Love |
| 6,494,909 B1 | 12/2002 | Greenhalgh |
| 6,500,202 B1 | 12/2002 | Shaolian et al. |
| 6,500,203 B1 | 12/2002 | Thompson et al. |
| 6,517,574 B1 | 2/2003 | Chuter |
| 6,520,983 B1 | 2/2003 | Colgan et al. |
| 6,520,984 B1 | 2/2003 | Garrison et al. |
| 6,530,947 B1 | 3/2003 | Euteneuer et al. |
| 6,533,806 B1 | 3/2003 | Sullivan et al. |
| 6,533,807 B1 | 3/2003 | Wolinsky et al. |
| 6,533,811 B1 | 3/2003 | Ryan et al. |
| 6,540,778 B1 | 4/2003 | Quiachon et al. |
| 6,554,858 B1 | 4/2003 | Dereume et al. |
| 6,562,063 B1 | 5/2003 | Euteneuer et al. |
| 6,592,544 B1 | 7/2003 | Mooney et al. |
| 6,602,280 B1 | 8/2003 | Chobotov |
| 6,695,875 B1 | 2/2004 | Stelter et al. |
| 6,733,521 B1 | 5/2004 | Chobotov et al. |
| 6,736,839 B1 | 5/2004 | Cummings |
| 6,761,733 B1 | 7/2004 | Chobotov et al. |
| 2001/0004706 A1 | 6/2001 | Hojeibane |
| 2001/0007954 A1 | 7/2001 | Shaolian et al. |
| 2001/0012943 A1 | 8/2001 | Shaolian et al. |
| 2001/0014823 A1 | 8/2001 | Ressemann et al. |
| 2001/0020184 A1 | 9/2001 | Dehdashtian et al. |
| 2001/0037142 A1 | 11/2001 | Stelter et al. |
| 2001/0047150 A1 | 11/2001 | Chobotov |
| 2001/0049534 A1 | 12/2001 | Lachat |
| 2002/0002397 A1 | 1/2002 | Martin et al. |
| 2002/0077692 A1 | 6/2002 | Besselink |
| 2002/0099405 A1 | 7/2002 | Yurek et al. |
| 2002/0099431 A1 | 7/2002 | Armstrong et al. |
| 2002/0099432 A1 | 7/2002 | Yee |
| 2002/0099433 A1 | 7/2002 | Fischell et al. |
| 2002/0099435 A1 | 7/2002 | Stinson |
| 2002/0099437 A1 | 7/2002 | Anson et al. |
| 2002/0103525 A1 | 8/2002 | Cummings |
| 2002/0111633 A1 | 8/2002 | Stoltze et al. |
| 2002/0111665 A1 | 8/2002 | Lauterjung |
| 2002/0111666 A1 | 8/2002 | Hart et al. |
| 2002/0111675 A1 | 8/2002 | Wilson |
| 2002/0116046 A1 | 8/2002 | DiCaprio et al. |
| 2002/0116047 A1 | 8/2002 | Vardi et al. |
| 2002/0120321 A1 | 8/2002 | Gunderson et al. |
| 2002/0123794 A1 | 9/2002 | Ellis et al. |
| 2002/0138081 A1 | 9/2002 | Blaeser et al. |
| 2002/0138127 A1 | 9/2002 | Stiger et al. |
| 2002/0138128 A1 | 9/2002 | Stiger et al. |
| 2002/0143381 A1 | 10/2002 | Gilligan et al. |
| 2002/0143383 A1 | 10/2002 | Parodi |
| 2002/0143387 A1 | 10/2002 | Soetikno et al. |
| 2002/0156489 A1 | 10/2002 | Gellman et al. |
| 2002/0165602 A1 | 11/2002 | Douglas et al. |
| 2002/0165603 A1 | 11/2002 | Thornton et al. |
| 2002/0173837 A1 | 11/2002 | Lauterjung |
| 2002/0177890 A1 | 11/2002 | Lenker |
| 2002/0183826 A1 | 12/2002 | Dorn et al. |
| 2002/0183827 A1 | 12/2002 | Derus et al. |
| 2002/0183832 A1 | 12/2002 | Penn et al. |
| 2002/0188341 A1 | 12/2002 | Elliott |
| 2002/0193863 A1 | 12/2002 | Rourke et al. |
| 2002/0193867 A1 | 12/2002 | Gladdish, Jr. et al |
| 2002/0193873 A1 | 12/2002 | Brucker et al. |
| 2002/0198587 A1 | 12/2002 | Greenberg et al. |
| 2002/0198588 A1 | 12/2002 | Armstrong et al. |
| 2003/0004560 A1 | 1/2003 | Chobotov et al. |
| 2003/0009211 A1 | 1/2003 | DiCarlo |
| 2003/0009212 A1 | 1/2003 | Kerr |
| 2003/0014101 A1 | 1/2003 | Harrison |
| 2003/0050684 A1 | 3/2003 | Abrams et al. |
| 2003/0050686 A1 | 3/2003 | Raeder-Devens |
| 2003/0074048 A1 | 4/2003 | Sherry |
| 2003/0074050 A1 | 4/2003 | Kerr |
| 2004/0073287 A1 | 4/2004 | Goicoechea et al. |
| 2004/0098079 A1 | 5/2004 | Hartley et al. |
| 2004/0098115 A1 | 5/2004 | Goicoechea et al. |
| 2004/0106974 A1 | 6/2004 | Greenberg et al. |
| 2004/0138734 A1 | 7/2004 | Chobotov et al. |

FOREIGN PATENT DOCUMENTS

EP 0 664 107 A1 7/1995

| | | |
|---|---|---|
| EP | 0 792 627 A2 | 9/1997 |
| EP | 0 821 979 A2 | 2/1998 |
| EP | 0 943 302 A2 | 9/1999 |
| EP | 1 093 772 A2 | 4/2001 |
| EP | 0 808 140 B1 | 12/2001 |
| EP | 1 208 817 A2 | 5/2002 |
| EP | 1 212 987 A2 | 6/2002 |
| EP | 1 212 988 A2 | 6/2002 |
| EP | 1 212 989 A2 | 6/2002 |
| EP | 1 327 422 A1 | 7/2003 |
| WO | 96/24308 | 8/1996 |
| WO | 98/07388 | 2/1998 |
| WO | 98/27894 | 7/1998 |
| WO | 98/36708 | 8/1998 |
| WO | 98/41167 | 9/1998 |
| WO | 99/11199 | 3/1999 |
| WO | 99/39662 | 8/1999 |
| WO | 99/43378 | 9/1999 |
| WO | 99/43379 | 9/1999 |
| WO | 99/65419 | 12/1999 |
| WO | 00/13613 | 3/2000 |
| WO | 00/33769 | 6/2000 |
| WO | 00/42947 | 7/2000 |
| WO | 00/42948 | 7/2000 |
| WO | 00/53251 | 9/2000 |
| WO | 01/58387 | 8/2001 |
| WO | 01/67993 | 9/2001 |
| WO | 01/74270 | 10/2001 |
| WO | 02/056798 | 7/2002 |
| WO | 02/060345 | 8/2002 |
| WO | 02/087651 | 11/2002 |
| WO | 03/008005 | 1/2003 |
| WO | 03/022181 | 3/2003 |
| WO | 04/002371 | 1/2004 |
| WO | 04/021932 | 3/2004 |

* cited by examiner

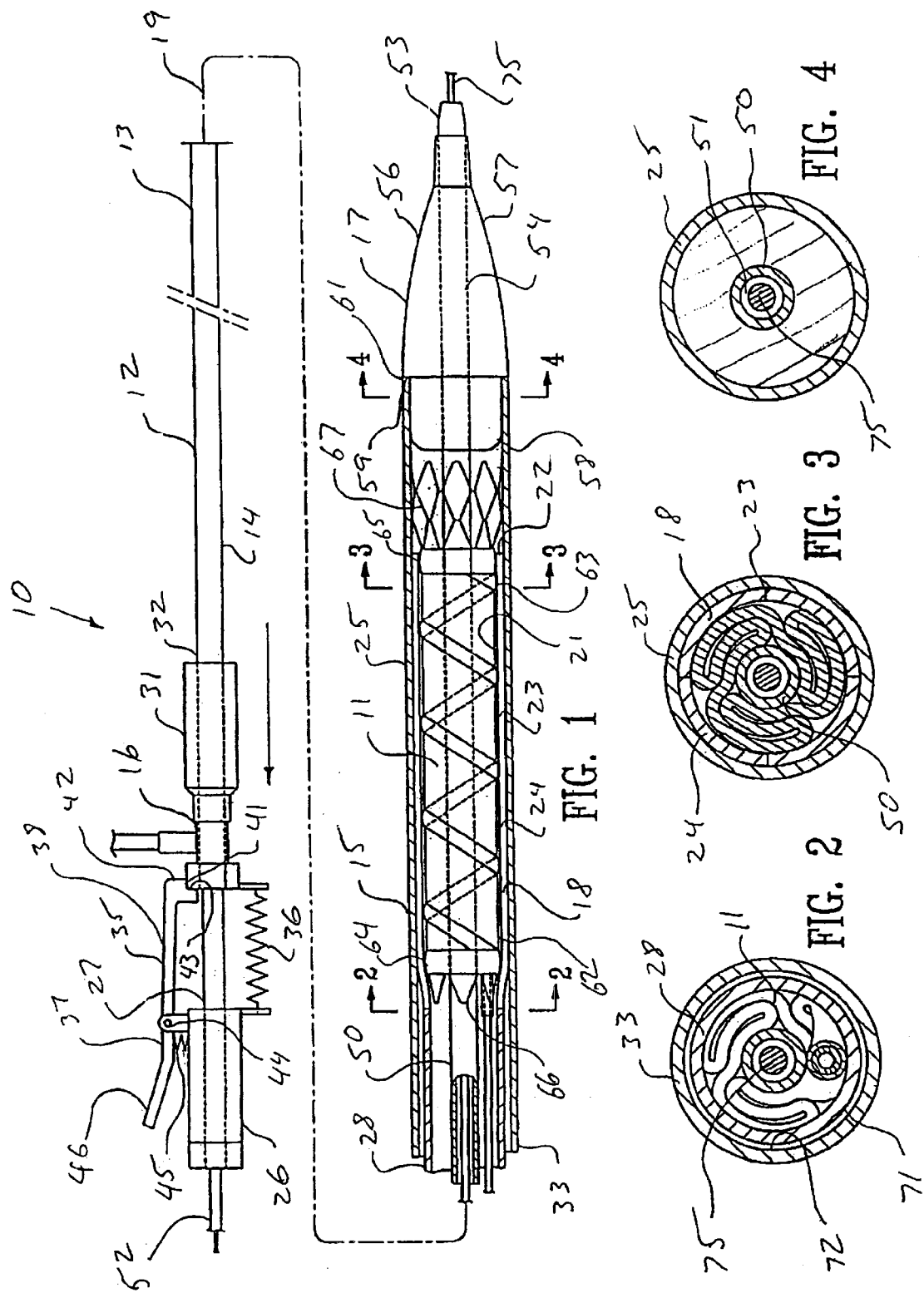

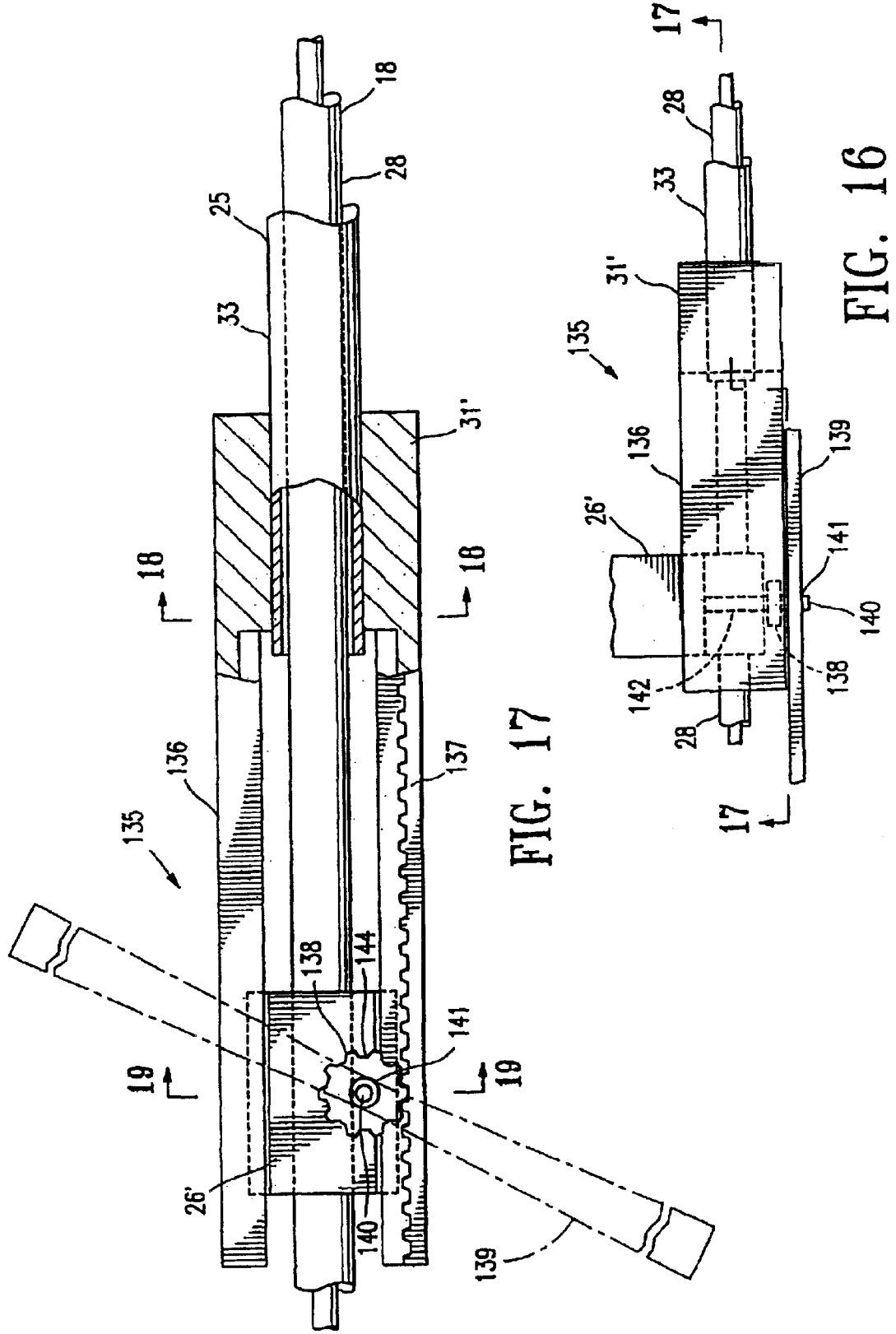

DELIVERY SYSTEM AND METHOD FOR EXPANDABLE INTRACORPOREAL DEVICE

RELATED APPLICATIONS

The present application is a divisional application of U.S. patent application Ser. No. 09/774,733 filed Jan. 31, 2001, now U.S. Pat. No. 6,602,280, which claims the benefit of priority from U.S. Provisional Patent Application No. 60/179,812 filed on Feb. 2, 2000, which are incorporated herein in its entirety.

BACKGROUND

The present invention relates to a system and method for the treatment of disorders of the vasculature. More specifically, the present invention relates to a system and method for treatment of thoracic or abdominal aortic aneurysm and the like, which is a condition manifested by expansion and weakening of the aorta. Such conditions require intervention due to the severity of the sequelae, which frequently is death. Prior methods of treating aneurysms have consisted of invasive surgical methods with graft replacement within the affected vessel as a reinforcing member of the artery. However, such a procedure requires a surgical cut down to access the vessel, which in turn can result in a catastrophic rupture of the aneurysm due to the decreased external pressure from the surrounding organs and tissues, which are moved during the procedure to gain access to the vessel. Accordingly, surgical procedures have a high mortality rate due to the possibility of the rupture discussed above in addition to other factors. Other factors can include poor physical condition of the patient due to blood loss, anuria, and low blood pressure associated with the aortic abdominal aneurysm. An example of a surgical procedure is described in a book entitled *Surgical Treatment of Aortic Aneurysms* by Denton A. Cooley, M.D., published in 1986 by W.B. Saunders Company.

Due to the inherent risks and complexities of surgical procedures, various attempts have been made in the development of alternative methods for deployment of grafts within aortic aneurysms. One such method is the noninvasive technique of percutaneous delivery by a catheter-based system. Such a method is described in Lawrence, Jr. et al. in "Percutaneous endovascular graft: experimental evaluation", *Radiology* (May 1987). Lawrence describes therein the use of a Gianturco stent as disclosed in U.S. Pat. No. 4,580,568. The stent is used to position a Dacron® fabric graft within the vessel. The Dacron graft is compressed within the catheter and then deployed within the vessel to be treated. A similar procedure has also been described by Mirich et al. in "Percutaneously placed endovascular grafts for aortic aneurysms: feasibility study," *Radiology* (March 1989). Mirich describes therein a self-expanding metallic structure covered by a nylon fabric, with said structure being anchored by barbs at the proximal and distal ends.

One of the primary deficiencies of the existing percutaneous devices and methods has been that the grafts and the delivery catheters used to deliver the grafts are relatively large in profile, often up to 24 French and greater, and stiff in bending. The large profile and bending stiffness makes delivery through the irregular and tortuous arteries of diseased vessels difficult and risky. In particular, the iliac arteries are often too narrow or irregular for the passage of a percutaneous device. Because of this, noninvasive percutaneous graft delivery for treatment of aortic aneurysm is not available to many patients who would benefit from it.

What has been needed is an endovascular graft and delivery system for the graft which has a small outer diameter and high flexibility to facilitate percutaneous delivery in patients who require such treatment. What has also been needed is a delivery system for an endovascular graft which is simple, reliable and can accurately deploy an endovascular graft within a patient's body.

SUMMARY

The invention is directed generally to a catheter for delivery of a variety of expandable intracorporeal devices, specifically, an endovascular graft which can be self expanding. The catheter can have an elongate shaft with a proximal section, a distal section, a proximal end and a distal end. The distal section of the elongate shaft can have a radially expandable shear barrier disposed about an inner space which is configured to accept an expandable intracorporeal device in a collapsed state. The catheter can be used for delivery and deployment of any appropriate expandable intracorporeal device. Typically, the catheter is used to deliver and deploy an expandable endovascular device such as a graft or stent graft. An outer radially constraining section is disposed about and radially constraining at least a portion of the radially expandable shear barrier and is capable of axial movement relative to the radially expandable shear barrier so as to controllably remove the radial constraint and allow the expandable intracorporeal device to deploy. Typically, the catheter is configured for percutaneous delivery from outside a patient to a desired site within a patient's body through an intracorporeal conduit or tissue of the patient.

In one embodiment, the radially expandable shear barrier and the outer radially constraining section are mechanically coupled to at least one terminal member disposed at the proximal end of the elongate shaft such that relative axial movement of the radially expandable shear barrier and outer radially constraining section can be carried out by an operator manipulating the terminal member at the proximal end of the elongate shaft. An actuator can be mechanically coupled to the at least one terminal member such that controllable and automatic relative axial movement between the radially expandable shear barrier and outer radially constraining section of the distal section of the elongate shaft can be carried out by activation of the actuator.

In another embodiment, the radially expandable shear barrier is in the form of a slitted inner tubular section having a generally tubular configuration and a distal end with at least one longitudinal slit extending proximally from the distal end. The slitted inner tubular member has an inner lumen disposed within it which is configured to accept at least a portion of an expandable intracorporeal device in a collapsed state. An outer tubular section is disposed about and radially constrains at least a portion of the slitted inner tubular section. The outer tubular section is capable of axial movement relative to the slitted inner tubular section in order to remove the radial constraint and allow the expandable intracorporeal device to deploy. The slitted inner tubular section and the outer tubular section can be mechanically coupled to at least one terminal member disposed at the proximal end of the elongate shaft such that relative movement of the inner and outer tubular sections can be carried out by an operator manipulating the at least one terminal member at the proximal end of the elongate shaft. Alternatively, the slitted inner tubular section can be mechanically coupled to a first terminal member consisting of a proximal handle disposed at the proximal end of the elongate shaft. The outer tubular section can be mechanically coupled to a second terminal member consisting of a distal handle disposed at the proximal end of the elongate shaft. Relative movement between the slitted inner tubular section and the outer tubular section can be carried out by imparting relative axial movement on the proximal and distal handles.

In yet another embodiment, a guidewire tube is disposed within the inner lumen of the slitted inner tubular section and has an inner guidewire lumen, a proximal end, a distal end and a distal section. A distally tapered nose piece can be disposed about and secured to the distal section of the guidewire tube. Optionally, the nosepiece disposed about a distal section of the guidewire tube can have a distal end with a contoured distally tapered bullet shape. The nosepiece can have a proximal end which is configured to engage the inner lumen of the distal end of the outer tubular section and produce a substantially smooth outer surface at the junction between the distal end of the outer tubular section and the nose piece.

The invention is also directed to a method for deploying an expandable intracorporeal device within a patient's body. A catheter system suitable for use with the method has an elongate shaft having a proximal section, a distal section, a proximal end and a distal end. The distal section of the elongate shaft has a radially expandable shear barrier disposed about an inner space configured to accept the expandable intracorporeal device in a collapsed state. An outer radially constraining section is disposed about and radially constrains at least a portion of the radially expandable shear barrier and which is capable of axial movement relative to the radially expandable shear barrier member in order to remove the radial constraint and allow the expandable intracorporeal device to deploy.

An expandable intracorporeal device is disposed within the inner space of the radially expandable shear barrier. As discussed above, such a catheter can be used for delivery and deployment of any appropriate expandable intracorporeal device. Typically, the catheter is used to deliver and deploy an expandable endovascular device such as a graft or stent graft. The distal end of the catheter system is introduced into the patient's body and advanced to a desired site within the patient's body. Various forms of guidance are suitable, including advancing the catheter over a guidewire or the use of a deflecting or steerable distal tip on the catheter. The catheter can be imaged during the procedure with fluoroscopic imaging, MRI, ultrasound or any other suitable form of imaging. In order to facilitate such imaging techniques, it may be desirable to place markers on the catheter or expandable intracoporeal device that enhance such techniques, such as radiopaque markers, ultrasound enhancement markers, isotopes or the like.

Once the distal section of the catheter and collapsed expandable intracorporeal device disposed within the catheter are located in a desired position, the expandable intracorporeal device is deployed. Deployment of the expandable intracorporeal device can be carried out in one embodiment of the invention by initiating relative axial movement between the radially expandable shear barrier and the outer constraining section. The relative movement sequentially removes the radial constraint on the radially expandable shear barrier to allow the expandable intracorporeal device to expand and deploy at the desired site.

In another embodiment of the method, a catheter is used wherein the radially expandable shear barrier is in the form of a slitted tubular section and the outer radially constraining section comprises an outer tubular section. Relative axial movement between the slitted inner tubular section and the outer tubular section can be carried out by axially withdrawing the outer tubular section from the slitted tubular section in a proximal direction. In addition, it may be desirable to deploy an expandable intracorporeal device which is an expandable endovascular graft having an expandable anchor portion disposed at a longitudinal extremity of the graft. With such a graft, the expandable anchor portion can be disposed within an inner lumen of the outer tubular section distal of a distal end of the slitted inner tubular section prior to deployment. Initiation of relative axial movement between the slitted inner tubular section and the outer tubular section can then be carried out to first relieve radial constraint on the expandable anchor portion and then sequentially the slitted inner tubular section.

BRIEF DESCRIPTION OF THE DRAWINGS

FIG. 1 shows an elevational view in partial section of a catheter system having features of the invention.

FIG. 2 is a transverse cross sectional view of the catheter system of FIG. 1 taken along lines 2—2 of FIG. 1.

FIG. 3 is a transverse cross sectional view of the catheter system of FIG. 1 taken along lines 3—3 of FIG. 1.

FIG. 4 is a transverse cross sectional view of the catheter system of FIG. 1 taken along lines 4—4 of FIG. 1.

FIG. 16 shows a top view of an alternate embodiment of an actuator device.

FIG. 17 shows an elevational view in partial section of the actuator device shown in FIG. 16.

DETAILED DESCRIPTION

Figure 5:
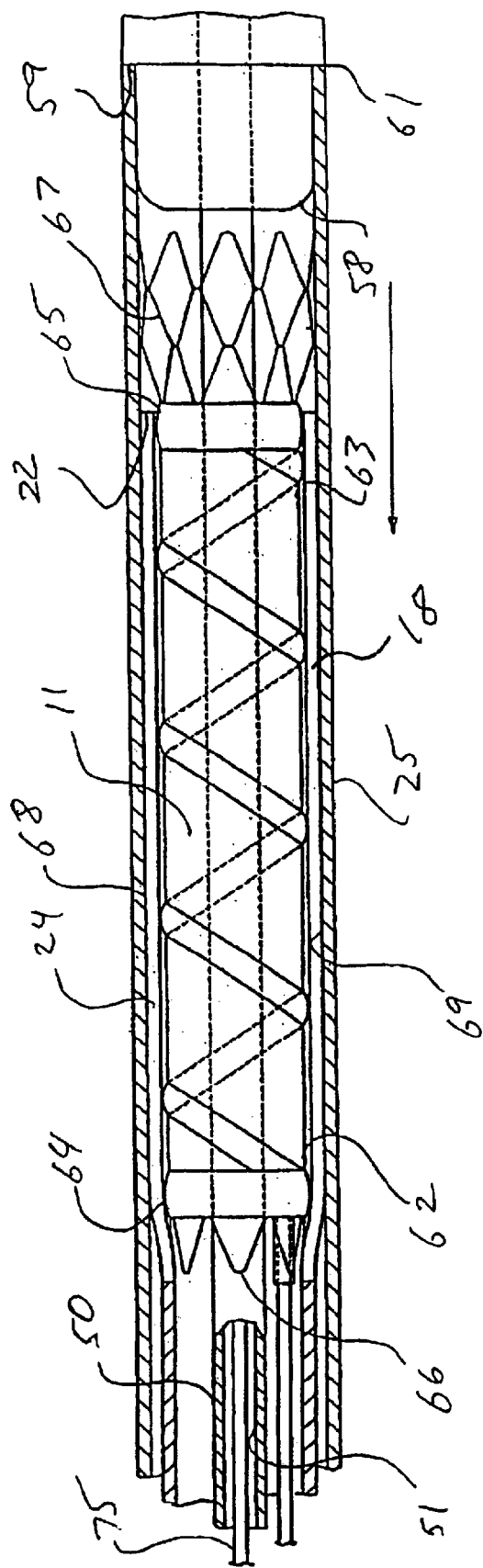
FIG. 5 is an enlarged view in partial section of a portion of the catheter system of FIG. 1.

FIGS. 1–5 illustrate a catheter system 10 having features of the invention. The catheter system 10 includes an expandable endovascular graft 11 and a catheter 12. The catheter 12 has an elongate shaft 13 with a proximal section 14, a distal section 15, a proximal end 16, a distal end 17, and a longitudinal axis 19. The distal section 15 of the elongate shaft 13 has a radially expandable shear barrier in the form of a slitted inner tubular section 18 disposed about an inner space or lumen 21 which is configured to accept the expandable endovascular graft 11 in a collapsed state. The slitted inner tubular section 18 can have a generally tubular configuration and a distal end 22 with four longitudinal slits 23 extending proximally from the distal end 22. The longitudinal slits 23 divide the slitted inner tubular section 18 into four petals 24. Although the longitudinal slits 23 are shown substantially parallel to the longitudinal axis 19 of the catheter 12, the slits 23 may be helical or underlating or have any other desired configuration. Also, the slits 23 need not extend completely through the slitted inner tubular section 18 and may only partially penetrate the wall of the slitted inner tubular section 18 so as to create fracture lines therein. The number of slits 23 can vary widely from about 1 to about 20, specifically about 2 to about 6. The catheter 12 can be configured and used for delivery and deployment of any appropriate expandable intracorporeal device.

An outer radially constraining section having an outer tubular section 25 is disposed about and radially constrains the slitted inner tubular section 18 and is capable of axial movement relative to the slitted inner tubular section 18. Typically, the catheter system 10 is configured for percutaneous delivery from outside a patient to a desired site within a patient's body through an intracorporeal conduit or tissue of the patient.

The slitted inner tubular section 18 is mechanically coupled to a first terminal member 26 disposed at the proximal end 16 of the elongate shaft 13. For the embodiment shown in FIGS. 1–5, the first terminal member is a proximal handle 26 on the proximal end 27 of an inner tubular member 28. The inner tubular member 28 may be a continuation of the slitted inner tubular section 18 as shown. The outer tubular section 25 is mechanically coupled to a second terminal member which is a distal handle 31 disposed on the proximal end 32 of an outer tubular member 33. The outer tubular member 33 can be an extension of the outer tubular section 25 as shown. Relative axial movement of the slitted inner tubular section 18 and outer tubular section 25 can be carried out by an operator manipulating the proximal and distal handles 26 and 31 at the proximal end 16 of the elongate shaft 13.

As is apparent from the figures, relative axial movement between the slitted inner tubular section 18 and the outer tubular section 25 could also be carried out by manipulation of the proximal end 27 of the inner tubular member 28 and the proximal end 32 of the outer tubular member 33 without the need for proximal and distal handles 26 and 31. Generally, relative axial movement between the slitted inner tubular section 18 and the outer tubular section 25 is carried out by proximally retracting the outer tubular section 25 relative to the slitted inner tubular section 18 so as to preserve the axial position of the expandable endovascular graft 11 relative to the desired deployment site within the patient during deployment.

An actuator 35 is optionally mechanically coupled to the terminal members 26 and 31. The actuator 35 provides controllable and automatic relative axial movement between the slitted inner tubular section 18 and outer tubular section 25 by activation of the actuator 35. The actuator 35 shown in FIG. 1 has an actuator spring 36 and an activation trigger 37. The actuator spring 36 is mechanically coupled to the and second terminal members, i.e. the proximal and distal handles 26 and 31 so as to provide a restoring force which tends to move the terminal members 26 and 31 closer together. The activation trigger 37 has an arm 38 with a notch 41 on a distal end 42 of the arm 38. The notch 41 is configured to engage the distal handle 31 with a contact surface 43. The arm 38 has a pivot point 44 which is pivotally secured to the proximal handle 26. An arm spring 45 keeps the notch 41 of the arm 38 engaged with the distal handle 31 so that the contact surface 43 prevents relative axial movement between the proximal handle 26 and the distal handle 31. When an activation portion 46 of the arm 38 is depressed radially inwardly relative to the proximal handle 26, the contact surface 43 disengages the distal handle 31 and the restoring force of the actuator spring 36 causes automatic relative axial movement between the proximal hand 26 and the distal handle 31. The spring 36 can be chosen to provide rapid automatic relative axial movement between the proximal and distal handles 26 and 31.

A guidewire tube 50 is disposed within the inner lumen 21 of the slitted inner tubular section 18 and inner tubular member 28 and has an inner guidewire lumen 51, a proximal end 52, a distal end 53 and a distal section 54. A distally tapered nose piece 56 is disposed about and secured to the distal section 54 of the guidewire tube 50. Optionally, the nosepiece 56 can have a distal end 57 with a contoured distally tapered bullet shape. In addition, the nosepiece 56 can have a proximal end 58 which can also be tapered to a bullet shape and a shoulder portion 59 configured to engage the inner lumen of the distal end of the outer tubular section 25 or alternatively, the inner lumen 21 of the distal end 22 of the slitted inner tubular section 18. In the alternative, when the slitted inner tubular section 18 is in a constrained state, there is preferentially a smooth outer surface 61 at the junction between the distal end 22 of the slitted inner tubular section 18 and the nosepiece 56.

The outer tubular section 25 of the distal section 15 can have an outside transverse dimension of about 1 to about 6 mm, specifically about 2 to about 5 mm, and more specifically about 2 to about 4 mm. The outer tubular section 25 can have a wall thickness of about 0.002 to about 0.02 inch, specifically about 0.004 to about 0.015 inch, further such as 0.005 to about 0.010 inch. Suitable materials for the outer tubular section include fluoropolymers such as Teflon®, polyethylene, Nylon, PEEK and the like. The overall length of the catheter system 10 can be from about 50 to about 150 cm, specifically about 75 to about 100 cm. In alternate embodiments the overall length of the catheter system 10 can be from about 75 to about 200 cm, specifically about 100 to about 135 cm. The slitted inner tubular section 18, inner tubular member 28 and outer tubular member 33 can have dimensions and materials similar to those of the outer tubular section 25 discussed above; however, an outside transverse dimension of the slitted inner tubular section 18 and inner tubular member 28 is typically configured to be slidably received within an inside transverse dimension of the outer tubular section 25 and outer tubular member 33. The longitudinal slits 23 of the slitted inner tubular section 18 can have a length of about 15 to about 150 mm, specifically about 15 to 140 mm, more specifically about 50 to about 100 mm, commensurate with the longitudinal dimension of the endovascular graft 11 contained within the distal end of the inner tubular member 28. Both the slitted inner tubular section 18 and outer tubular section 25 typically have rounded transverse cross sections, although an oval shape and other shapes are possible.

The expandable endovascular graft 11 is disposed within the inner lumen 21 of the slitted inner tubular section 18. A suitable expandable endovascular graft for delivery and deployment at a desired site within a patient is disclosed in U.S. Pat. No. 6,395,019, to M. Chobotov, which is hereby incorporated by reference in its entirety. The expandable endovascular graft 11 has a proximal end 62, a distal end 63, a proximal inflatable cuff 64, a distal inflatable cuff 65, a proximal anchor member 66 and a distal anchor member 67. As defined herein, the proximal end 16 of the catheter 12 is the end proximal to the operator of the catheter and the distal end 17 of the catheter 12 is the portion which enters and extends into the patient's body. The proximal direction for the catheter 12 and expandable endovascular graft 11 are the same. This convention is used throughout the specification for the purposes of clarity, although other conventions are commonly used. For example, another useful convention is one defined where the proximal end of an endovascular graft is that end of the graft which is proximal to the source of blood flow. Such a convention is used in U.S. Pat. No. 6,395,019, although that convention is not adopted herein.

The endovascular graft 11 of FIG. 1 is shown in an idealized non-collapsed state which has been reduced in scale for purposes of clarity of the drawing. FIGS. 2 and 3 show transverse cross sections of the expandable endovascular graft 11 in a folded or collapsed state within the inner lumen 21. However, although FIGS. 2 and 3 show a more realistic illustration of the expandable endovascular graft 11 in a collapsed state than FIG. 1, the configuration of the graft 11 shown in FIGS. 2 and 3 is still somewhat idealized. Typically, an expandable endovascular graft 11 in a collapsed state that is suitable for percutaneous delivery to and deployment within a patient's abdominal aorta would have a large number of folds and overlaps rather than the several folds and overlaps shown in FIGS. 2 and 3. Also, the endovascular graft 11 is likely to be tightly packed into the inner lumen 21 in order to achieve the desired low profile of the distal section 15 of the catheter 12 for percutaneous delivery of the catheter system 10. Outward radial force results from the tight packing of the endovascular graft 11 which is illustrated in FIG. 5 where the outside surface 68 of the slitted inner tubular section 18 makes contact with the inside surface 69 of the outer tubular section 25. In FIG. 2 a gap is shown between the outside surface 71 of the inner tubular member 28 and the inside surface 72 of the outer tubular member 33 to allow ease of relative axial movement therebetween.

In use, the distal end 17 of the catheter system 10 is introduced into the patient's body and advanced to a desired site within the patient's body. Various forms of guidance are suitable including advancing the catheter 12 over a guidewire 75 or the use of a deflecting or steerable distal tip on the catheter 12. The catheter 12 can be imaged during the procedure with fluoroscopic imaging, MRI, ultrasound or any other suitable form of imaging. In order to facilitate such imaging techniques, it may be desirable to place markers (not shown) on the catheter 12 or expandable endovascular graft 11 that enhance such techniques, such as radiopaque markers, ultrasound enhancement markers, isotopes or the like.

Figure 6:
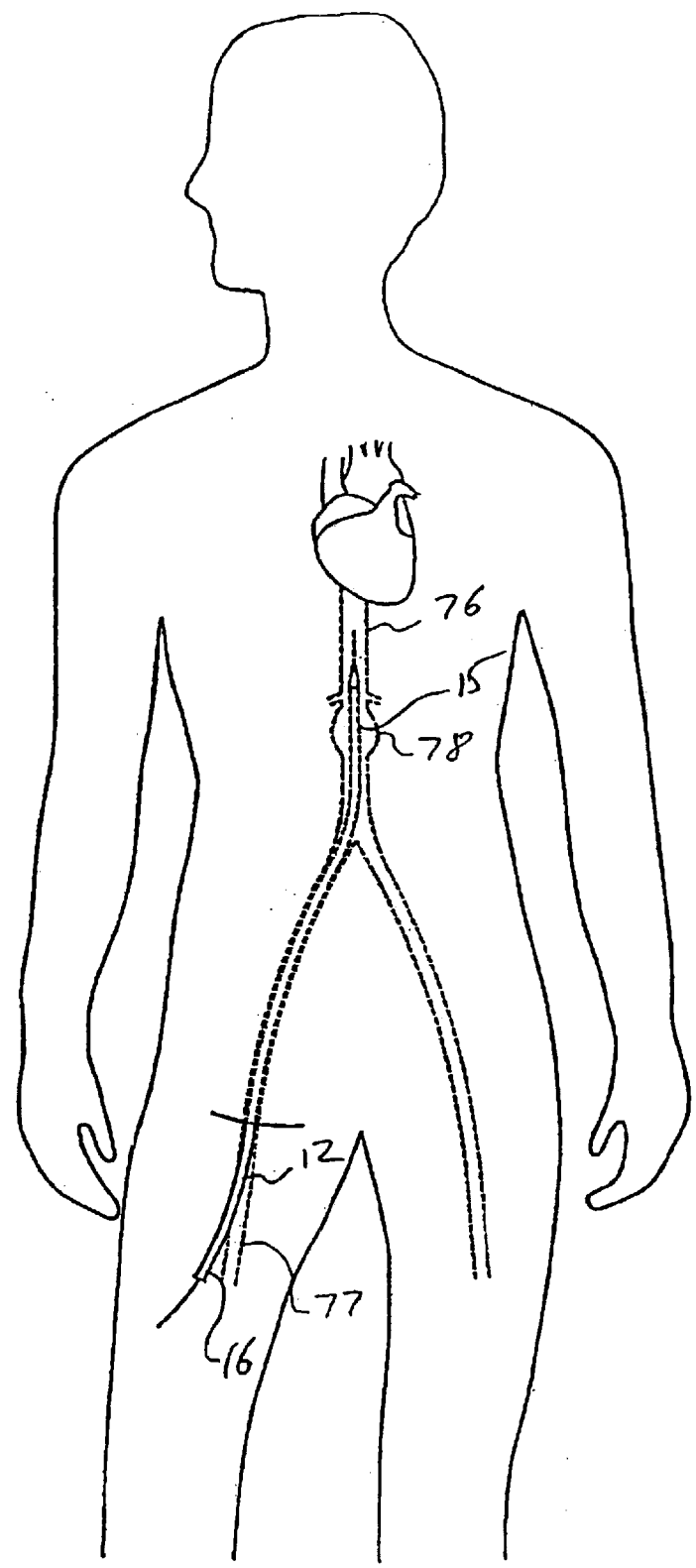
FIG. 6 is a schematic view of the catheter system of FIG. 1 disposed within the vasculature of a patient.

Referring to FIG. 6, the catheter system 10 of FIGS. 1–5 is shown disposed within a patient's vasculature, specifically, with the distal section 15 of the catheter 12 disposed within the patient's abdominal aorta 76. The proximal end 16 of the catheter 12 is shown exiting the patient's femoral artery 77 for manipulation by an operator of the catheter system 10. The distal section 15 of the catheter 12 is positioned adjacent an abdominal aortic aneurysm 78.

Figure 7:
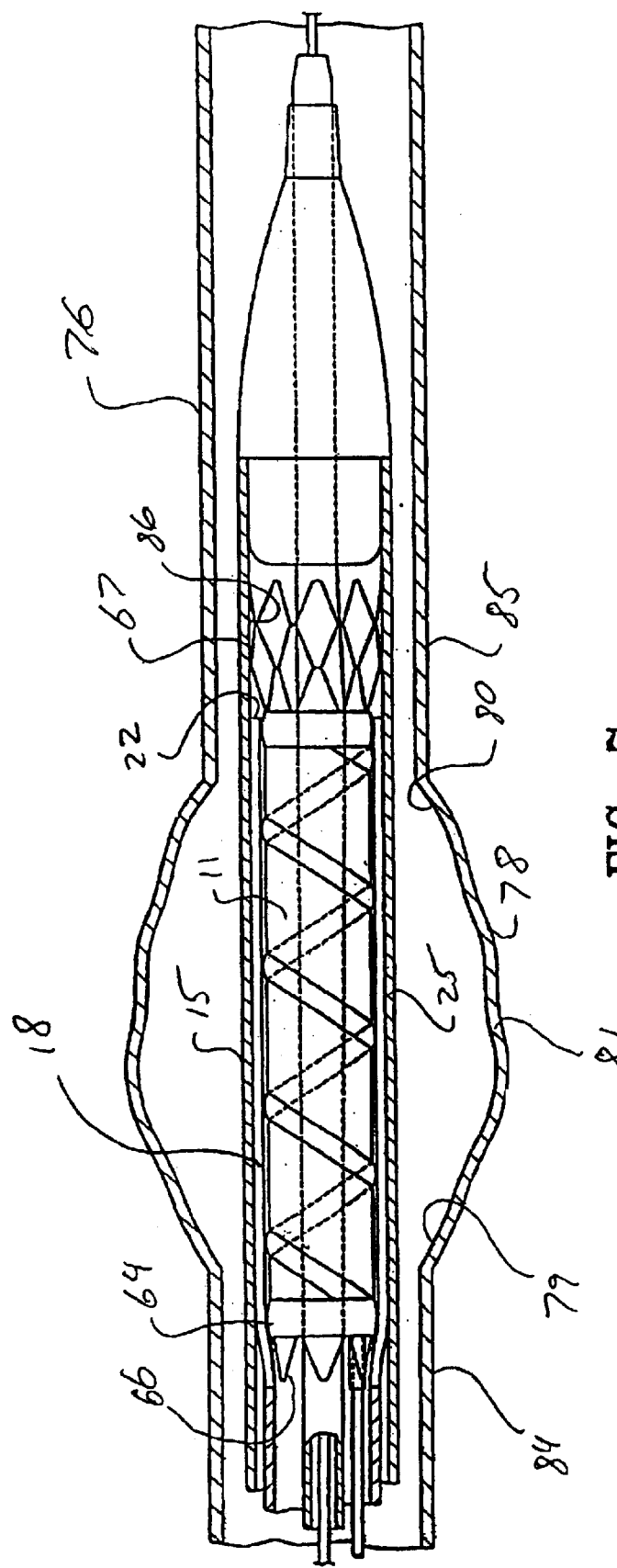
FIG. 7 illustrates an enlarged view of a distal portion of the catheter system of FIG. 6 disposed adjacent an abdominal aortic aneurysm of the patient.

FIG. 7 depicts an expanded view of the patient's abdominal aorta 76 and the aneurysm 78 with the distal section 15 of the catheter 12 disposed therein. The aneurysm 78 has a proximal end 79, a distal end 80 and a midsection 81. The graft 11 is positioned such that the proximal anchor member 66 and proximal inflatable cuff 64 are disposed within a first relatively healthy portion 84 of the patient's aorta 76 proximally adjacent the proximal end 79 of the aneurysm 78. Likewise, the distal anchor member 67 of the expandable endovascular graft 11 is positioned in a second relatively healthy portion 85 of the patient's aorta 76 distal of the distal end 80 of the aneurysm 78. The distal anchor member 67 of the graft 11 is optionally disposed within an inner lumen 86 of the outer tubular section 25 distal of the distal end 22 of the slitted inner tubular section 18 prior to deployment. Initiation of relative axial movement between the slitted inner tubular section 18 and the outer tubular section 25 can then be carried out to first relieve radial constraint on the distal anchor member 67 and then subsequently the slitted inner tubular section 18.

Once the distal section 15 of the catheter 12 and the expandable endovascular graft 11 are located in a desired position, the expandable endovascular graft 11 is deployed. Deployment of the expandable endovascular graft 11 can be carried out by initiating relative axial movement between the slitted inner tubular section 18 and the outer tubular section 25. The relative movement sequentially removes the radial constraint of the outer tubular section 25 on the slitted inner tubular section 18 to allow the expandable endovascular graft 11 to expand and deploy at the desired site. The slitted inner tubular section 18 can receive support from buckling by the graft 11, and the inner tubular section 18 in turn isolates graft 11 from shear and compressive forces created by relative motion of the outer tubular section 25 against the inner tubular section 18.

Figure 8:
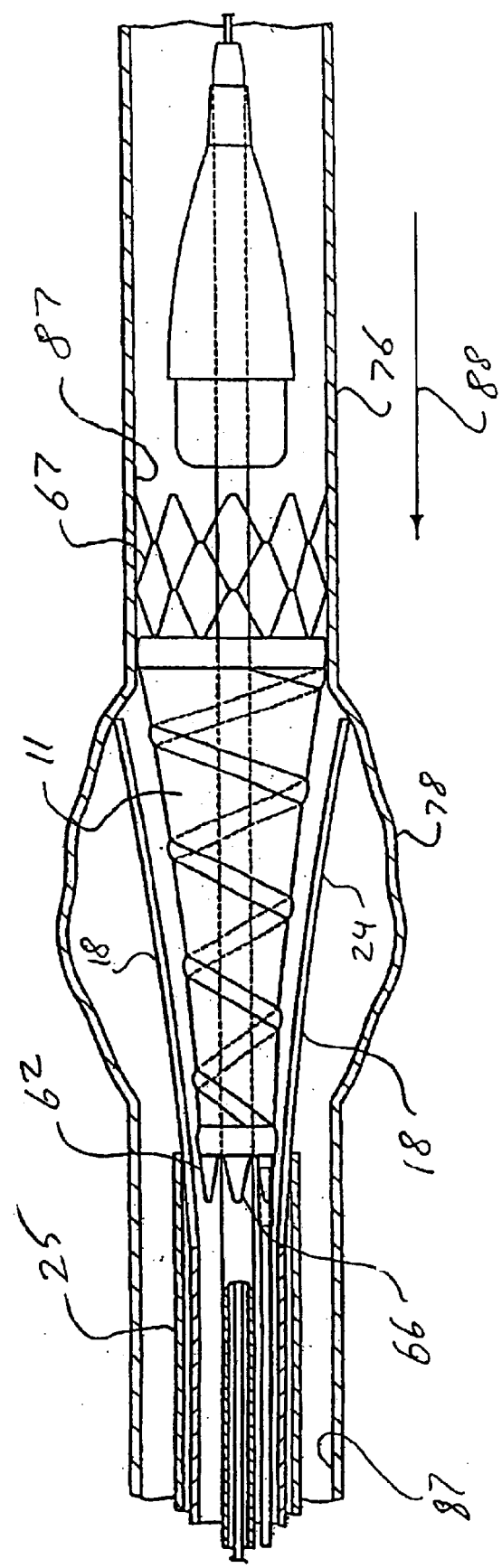
FIG. 8 illustrates the catheter system of FIG. 6 in the initial stages of deployment.
Figure 9:
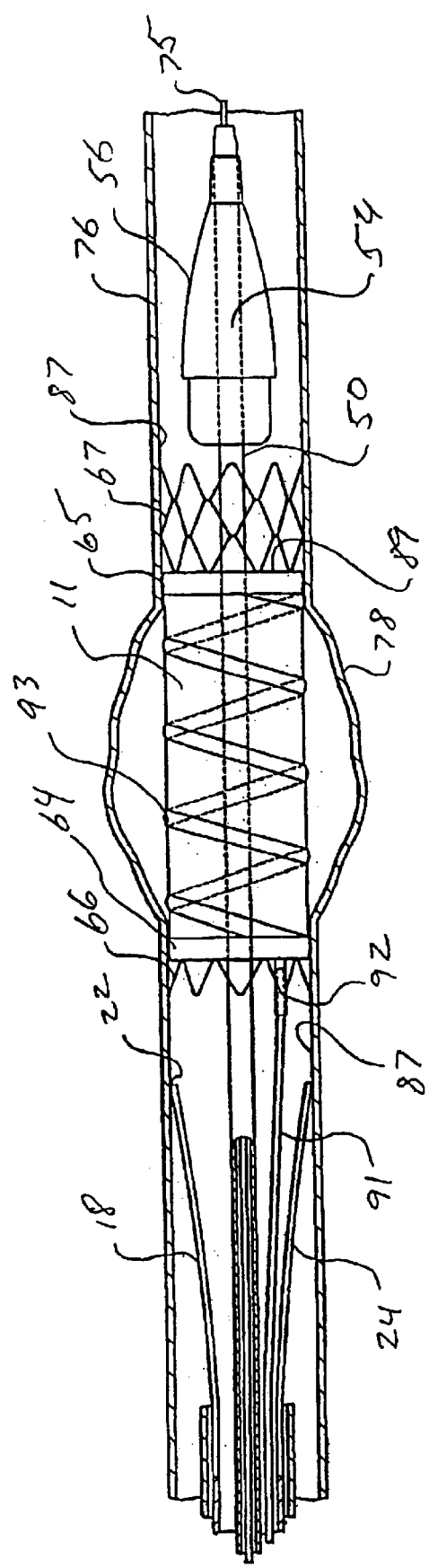
FIG. 9 illustrates the catheter system of FIG. 6 with the expandable endovascular graft in a stage of further deployment relative to FIG. 8.
Figure 10:
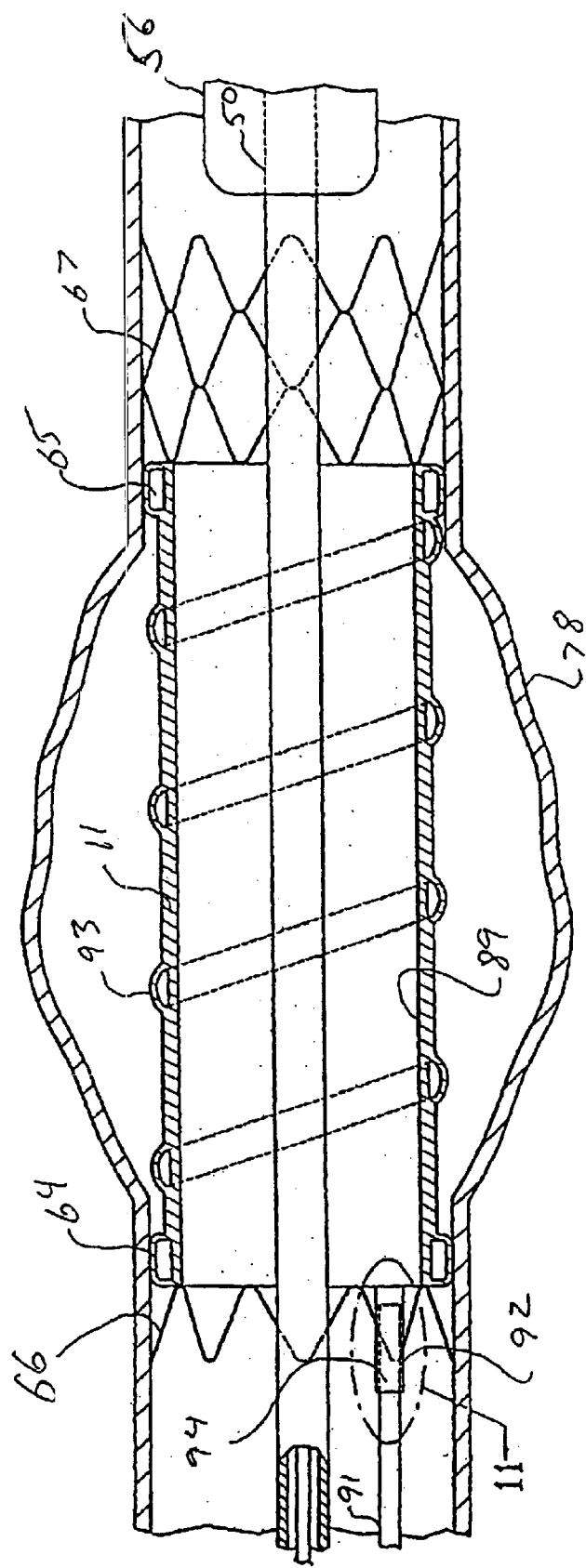
FIG. 10 is a more detailed view of the catheter system of FIG. 9 showing the expandable endovascular graft in partial longitudinal section.

Referring to FIG. 8, the outer tubular section 25 has been partially retracted in a proximal direction relative to the slitted inner tubular section 18. As a result, the distal anchor member 67 of the expandable endovascular graft 11 has expanded radially so as to contact the inside surface 87 of the patient's aorta 76 and anchor thereto by frictional force. Once the distal anchor member 67 is expanded against the inside surface 87 of the patient's aorta 76, the force of the blood flow in a direction indicated by arrow 88 serves to fill the expandable endovascular graft 11 and aid in its deployment in an outward radial direction. The force of the blood flow into the distal end 63 of the expandable endovascular graft 11 is sufficient to fill the graft 11 but allows the petals 24 of the slitted inner tubular section 18 to be withdrawn in a proximal direction. Typically, during deployment of the graft 11, once the outer tubular section 25 has been withdrawn completely from the petals 24 of the slitted inner tubular section 18, thereby removing the radial constraint on the petals 24, the petals 24 may then be withdrawn in a proximal direction until the distal end 22 of the slitted inner tubular section 18 is disposed proximal to the proximal end 62 of the graft 11 as shown in FIGS. 9 and 10. This allows the optional proximal anchor member 66 of the graft 11 to deploy in an outward radial direction and engage the inside surface 87 of the patient's aorta 76. The petals 24 of the unconstrained slitted inner tubular section 18 can be pulled between the self expanding proximal anchor member 66 and the inside surface 87 of the patient's aorta 76 notwithstanding the frictional force created by the expansion of the anchor member 66. Once the petals 24 of the slitted inner tubular section 18 have been retracted, the graft 11 is mechanically deployed and can then be inflated. Prior to inflation of the graft 11, however, the nosepiece 56 and distal section 54 of the guidewire tube 50 are typically withdrawn in a proximal direction through an inner lumen 89 of the graft 11.

Thereafter, a desired inflation material (not shown) is pumped through the inflation tube 91 and into the injection port 92 of the graft 11 so as to fill the inflatable portions of the graft 11, including the proximal inflatable cuff 64, distal inflatable cuff 65 and longitudinal inflatable channel 93 to a desired pressure with a desired amount of inflation material. Normally, inflation material is injected to a pressure and amount that suffices to form a seal between the distal inflatable cuff 65 and the inside surface 87 of the patient's aorta 76.

Suitable inflation materials can include gas, fluid, particles, gel or any combination thereof. A fluid which sets, hardens or gels over time can also be used as an inflation material. The inflation material may contain a contrast medium which facilitates imaging of the device while being deployed within a patient's body. For example, radiopaque materials such as bismuth, barium, gold, platinum, tantalum or the like may be used in particulate or powder form to facilitate visualization of the graft under fluoroscopy. Fixed radiopaque markers may also be attached or integrally molded into the graft for the same purpose, and may be made from the same radiopaque materials discussed above.

Once a desired amount of inflatable material has been injected into the inflatable channels of the graft 11, a distal end 94 of the inflation tube 91 is disconnected from the injection port 92 by activation or removal of a retention wire 95 which serves to connect the distal end 94 of the inflation tube 91 with the injection port 92 of the graft 11.

Figure 12:
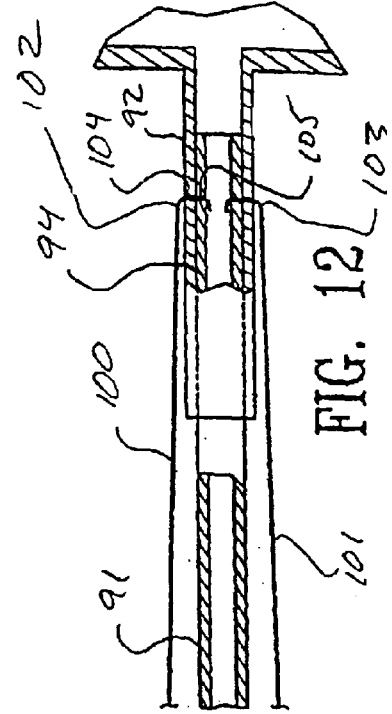
FIG. 12 is a view similar to that shown in FIG. 11 with an alternative embodiment of a detachable coupling having two retention wires removably disposed within locking holes of the distal end of the fill tube and the injection port.
Figure 11:
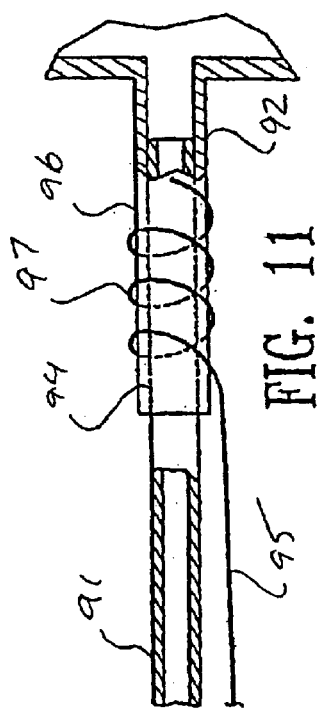
FIG. 11 is a detailed view of the circumscribed portion in FIG. 10 indicated at number 11 showing a detachable coupling of a distal end of a fill tube of the catheter and an injection port of the expandable endovascular graft which has a retention wire disposed about the coupling.

FIGS. 11 and 12 depict alternative embodiments of retention wires used to secure the distal end 94 of the inflation tube 91 to the injection port 92 of the graft 11. FIG. 11 illustrates a single retention filament or wire 95 which is helically wrapped about the outside surface 96 of the injection port 92 and distal end 94 of the inflation tube 91 disposed therein. The retention wire 95 has a preshaped coiled end 97 which has a nominal inside diameter which is less than an outside diameter of the injection port 92. As such, the coiled end 97 of the retention wire 95 compresses the junction of the distal end 94 of the inflation tube 91 and the injection port 92 so as to create a connection therebetween held in place by frictional force. The retention wire 95 is activated or deployed by pulling on a proximal end or section of the retention wire 95 so as to uncoil the coiled end 97 of the retention wire and remove the inward radial compressive force or constraint and thus the frictional force between the distal end 94 of the inflation tube 91 and the inside diameter of the injection port 92. Thereafter, the distal end 94 of the inflation tube 91 may be axially withdrawn from the injection port 92 without excessive frictional resistance, and i.e. not enough frictional resistance to dislodge the graft 11 from its axial position within the patient's aorta.

Typically, the retention wire extends from the injection port 92 proximally to the proximal end 16 of the catheter 12 through the inside lumen of the inner tubular member 28. In this way, an operator can disengage the inflation tube 91 from the injection port 92 by pulling on the proximal end of the retention wire 95 from a proximal end 16 of the catheter 12. The retention wire 95 can be a small diameter wire made from a material such as stainless steel or NiTi; in a particular embodiment of the invention, the retention wire 95 can be a spring formed of a variety of suitable spring materials. Alternatively the material of the retention wire may have a braided, stranded or single element, e.g. monofilament, configuration.

FIG. 12 shows another embodiment of a retention wire system wherein a first retention filament or wire 100 and a second retention filament or wire 101 have distal ends 102 and 103 respectively disposed within side holes 104 of the injection port 92 and side holes 105 of the distal end 94 of the inflation tube 91. The distal ends of the retention wires act to interlock the side holes 104 and 105 by creating a removable shear pin element which prevents relative axial movement between the distal end 94 of the inflation tube 91 and the injection port 92. The retention wires 100 and 101 are activated or deployed by pulling on a proximal portion of the retention wires so as to remove the distal ends 102 and 103 of the retention wires from the side holes 104 and 105 and thereby remove the shear pin function. Thereafter, relative movement between the distal end 94 of the inflation tube 91 and the injection port 92 is possible, and the distal end 94 of the inflation tube. 91 can be withdrawn from the injection port 92 without excessive axial force on the graft 11, i.e. without sufficient axial force on the graft 11 to dislodge the graft 11 from its position within the patient's artery 76 or other intracorporeal conduit.

Once the graft 11 has been inflated and the distal end 94 of the inflation tube 91 withdrawn from the injection port 92, the catheter 12 can then be withdrawn in a proximal direction. Once clear of the site of intervention within the patient's body, the catheter 12 can be removed from the patient's body altogether.

Figure 13:
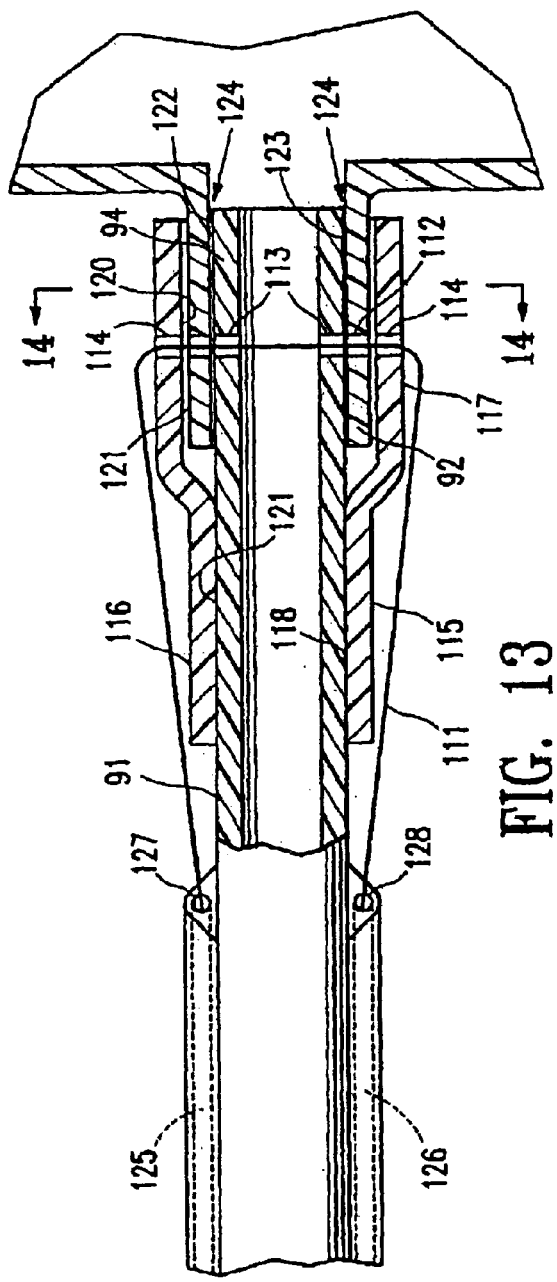
FIG. 13 is a view similar to that shown in FIG. 11 with another embodiment of a detachable coupling.

FIG. 13 shows yet another embodiment of a retention wire system wherein a retention filament or wire 111 is disposed within side holes 112 of the injection port 92, side holes 113 of the distal end 94 of the inflation tube 91 and side holes 114 of an outer shroud 115. The retention wire 111 acts to interlock the side holes 112 and 113 and 114 by creating a removable shear pin element which prevents relative axial movement between the distal end 94 of the inflation tube 91 and the injection port 92. The retention wire 111 is activated or deployed by pulling on a proximal portion of the retention wire 111 so as to remove the retention wire 111 from the side holes 112, 113 and 114 and thereby remove the shear pin function of the retention wire 111. Thereafter, relative axial movement between the distal end 94 of the inflation tube 91 and the injection port 92 is possible. Relative axial movement is also then possible between the outer shroud 115 and the injection port 92.

Outer shroud 115 is a tubular member having a proximal end 116 and a distal end 117. The proximal end 116 is necked down to an inside surface 118 which mates with and is secured to an outside surface 121 of the inflation tube 91. The distal end 117 of the shroud 115 has an inside diameter 120 configured to be slidably disposed and close fitting over an outside surface 121 of the inflation tube 91. The shroud 115 serves to prevent leakage at the coupling by preventing ballooning or expansion of the injection port 92 from pressure exerted by inflation material flowing through the coupling. In the embodiment of FIG. 13, as inflation material is forced through the inflation tube 91 and into the injection port 92, some inflation material may be forced into the junction between an outside surface 122 of the distal end of the inflation tube 91 and an inside surface 123 of the injection port 92 as indicated by arrows 124. As this happens, the interposed inflation material will tend to increase the outside diameter of the injection port 92 and force it into the inside diameter 120 of the distal end 117 of the shroud 115 forming a seal therebetween and preventing leakage of inflation material.

The inflation tube 91 may have a first elongated lumen 125 and a second elongated lumen 126 disposed along the sides of the inflation tube 91 to house the ends of the retention wire 111 within the lumens. The first and second elongated lumens can be terminated proximal to the distal end of the inflation tube 91 at a first distal port 127 and a second distal port 128. In this way, the retention wire 111 can be passed through the first elongated lumen 125 and exit the first distal port 127. The retention wire 111 can then be passed through the side holes 112, 113 and 114, so as to axially lock the inflation tube 91 to the injection port 92, and then back through the second distal port 128. The retention wire can have ends accessible at a proximal end of the inflation tube to permit fixation of or application of tension on the ends of the retention wire 111 during inflation and withdrawal of the retention wire 111 thereafter in order to decouple the distal end of the inflation tube. The first and second elongated lumens 125 and 126 keep the retention wire from being tangled or pinched which may impede withdrawal of the retention wire 111 and removal of the inflation tube 91 after the inflation process.

Figure 15:
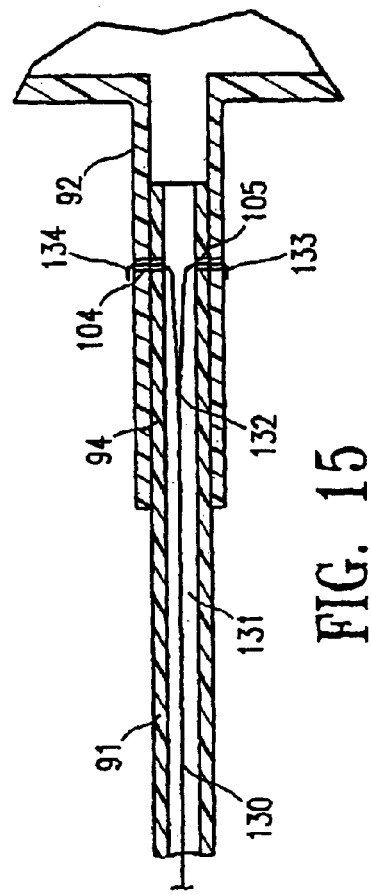
FIG. 15 is a view similar to that shown in FIG. 11 with another embodiment of a detachable coupling.
Figure 14:
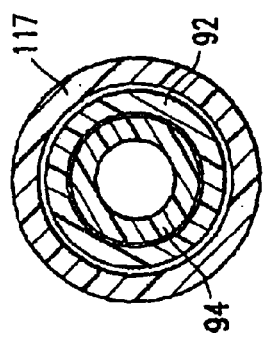
FIG. 14 is a transverse cross sectional view of the coupling of FIG. 13 taken along lines 14—14 in FIG. 13.
Figure 18:
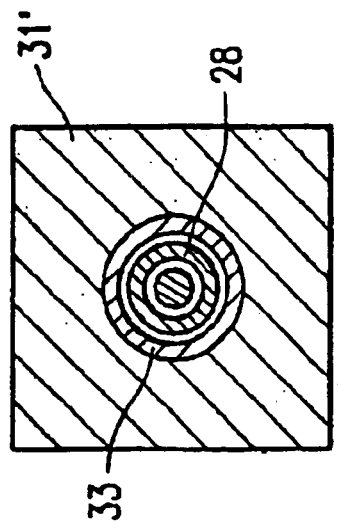
FIG. 18 is a transverse cross sectional view of the actuator device of FIG. 17 taken along lines 18—18 of FIG. 17.
Figure 19:
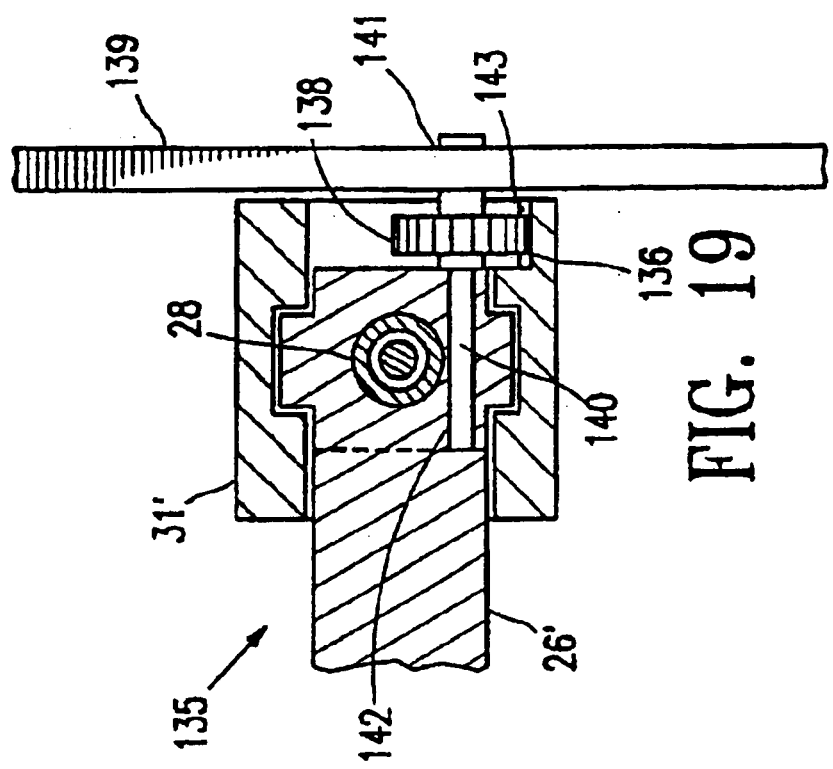
FIG. 19 is a transverse cross sectional view of the actuator device of FIG. 17 taken along lines 19—19 of FIG. 17.

FIG. 15 shows an additional alternative embodiment of a retention wire system used to secure the distal end of the inflation tube 91 to the injection port 92 of the graft 11 wherein a single retention filament or wire 130 is disposed within the lumen 131 of the inflation tube 91. The distal end 132 of the retention wire may have one or more loops 133 and 134, respectively, disposed within side holes 104 of the injection port 92 and side holes 105 of the distal end 94 of the inflation tube 91. The distal loops of the retention wire act to interlock the side holes 104 and 105 by creating a removable shear pin element which prevents relative axial movement between the distal end 94 of the inflation tube 91 and the injection port 92. Alternate embodiments may include multiple retention filaments or wires disposed within the lumen 131 of the inflation tube 91.

FIGS. 16–19 show an alternate embodiment of an actuator 135 in which a manually activated rack and pinion mechanism 136 can be mechanically coupled to the terminal members 26' and 31' and can be used to employ relative motion between the terminal members 26' and 31'. The rack and pinion mechanism 136 provides controllable and automatic relative axial movement between the slitted inner tubular section 18 and the outer tubular section 25 by activation of the mechanism 136. The rack and pinion mechanism 136, as shown in FIG. 17 has a rack 137, a pinion 138 and a pinion handle 139 mechanically coupled to the first terminal member 26' with a pinion shaft 140. The pinion 138, pinion shaft 140 and the pinion handle 139 form a pinion handle assembly 141 which is rotatably coupled to the first terminal member 26' by the pinion shaft 140. The pinion handle 139 is secured to the pinion 138 by the pinion shaft 140 to prevent relative rotational movement therebetween. As discussed above, the pinion shaft 140 is rotatably disposed within a cylindrical pinion cavity 142 disposed within the first terminal member 26'. The rack 136 is secured to the second terminal member 31' which is secured to the outer tubular member 33. The rack contains a plurality of teeth 143 configured to operatively engage the notches 144 of the pinion 138 such that when the pinion handle assembly 141 is rotated there is controlled retraction of the outer tubular member 33 over the inner tubular member 28. Thus, the outer tubular section 25 is displaced relative to the slitted inner tubular section 18. The pinion handle 139 can be activated manually, or can optionally be actuated automatically with actuators such as a motor drive, spring drive or the like which can be chosen to provide a fixed amount of force over a given distance and rapid automatic relative axial movement between the first and second terminal members 26' and 31'.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A method for deploying an expandable intracorporeal device within a patient's body comprising:
   a) providing a catheter system including:
      an elongate shaft having a proximal section, a distal section, a proximal end and a distal end,
      the distal section of the elongate shaft comprising a radially expandable shear barrier disposed about an inner space of the elongate shaft configured to accept the expandable intracorporeal device in a collapsed state,
      an outer radially constraining section which is disposed about and radially constrains at least a portion of the radially expandable shear barrier,
      the expandable intracorporeal device disposed within the inner space of the radially expandable shear barrier, the expandable intracorporeal device comprising an injection port in fluid communication with an inflatable portion of the expandable intracorporeal device, and
      an injection lumen which is disposed within the inner space of the elongate shaft, wherein the injection lumen is configured to be removably coupled to the injection port;
   b) introducing the distal end of the catheter system into the patient's body;
   c) advancing the catheter system to a desired site within the patient's body;
   d) initiating relative axial movement between the radially expandable shear barrier and the outer constraining section to at least partially remove the radial constraint on the radially expandable shear barrier sufficiently for the expandable intracorporeal device to expand and deploy at the desired site, and
   e) injecting an inflation material through the injection lumen and into the injection port.

2. The method of claim 1 wherein the expandable intracorporeal device disposed within the inner space of the radially expandable shear barrier comprises an expandable endovascular device.

3. The method of claim 2 wherein the expandable endovascular device disposed within the inner space of the radially expandable shear barrier comprises an expandable endovascular graft.

4. The method of claim 1 wherein the radially expandable shear barrier comprises a slitted tubular section and the outer radially constraining section comprises an outer tubular section.

5. The method of claim 4 wherein the relative axial movement between the slitted inner tubular section and the outer tubular section comprises axially withdrawing the outer tubular section from the slitted tubular section in a proximal direction.

6. The method of claim 4 wherein the expandable intracorporeal device comprises an expandable endovascular graft having an expandable anchor portion disposed within an inner lumen of the outer tubular section distal of a distal end of the slitted inner tubular section prior to initiation of relative axial movement between the slitted inner tubular section and the outer tubular section.

7. The method of claim 1 wherein a maximum outside transverse dimension of the distal section of the elongate shaft is about 2.5 to about 6 mm prior to initiation of relative axial movement between the radially expandable shear barrier and the outer constraining section.

8. The method of claim 1 wherein a maximum outside transverse dimension of the distal section of the elongate shaft is about 2.5 to about 3.5 mm prior to initiation of relative axial movement between the radially expandable shear barrier and the outer constraining section.

9. A method for deploying an expandable endovascular graft within a patient's body comprising:
   providing a catheter system including:
      an elongate shaft having a proximal section, a distal section, a proximal end and a distal end,
      the distal section of the elongate shaft comprising a radially expandable shear barrier disposed about an inner space configured to accept the expandable endovascular graft in a collapsed state,
      an outer radially constraining section which is disposed about and radially constrains at least a portion of the radially expandable shear barrier, and
      an expandable endovascular grail disposed within the inner space of the radially expandable shear barrier, the endovascular grail comprising a distal inflatable cuff and a distal anchor member;
   introducing the distal end of the catheter system into the patient's vasculature;
   advancing the catheter system to a desired site within the patient's vasculature;
   initiating relative axial movement between the radially expandable shear barrier and the outer constraining section to a least partially remove the radial constraint on the radially expandable shear barrier;
   initiating radial expansion of the distal anchor member so as to contact the inside surface of the patient's vasculature, and
   initiating radial expansion of the distal inflatable cuff.

10. The method of claim 9 wherein the outer radially constraining section comprises an outer tubular section.

11. The method of claim 9 wherein the relative axial movement between the radially expandable shear barrier and the outer constraining section comprises axially withdrawing the outer constraining section from the radially expandable shear barrier in a proximal direction.

12. The method of claim 9 wherein a maximum outside transverse dimension of the distal section of the elongate shaft is about 2.5 to about 6 mm prior to initiation of relative axial movement between the radially expandable shear barrier and the outer constraining section.

* * * * *